United States Patent
Joshi et al.

(10) Patent No.: US 7,019,172 B2
(45) Date of Patent: Mar. 28, 2006

(54) PROCESS FOR PREPARATION OF S-(−)-BETAXOLOL AND SALTS THEREOF

(75) Inventors: Ramesh Anna Joshi, Maharashtra (IN); Muthukrishnan Murugan, Maharashtra (IN); Dinesh Ramesh Garud, Maharashtra (IN); Sanjay Pandurang Borikar, Maharashtra (IN); Mukund Keshav Gurjar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 55 days.

(21) Appl. No.: 10/879,500

(22) Filed: Jun. 30, 2004

(65) Prior Publication Data

US 2006/0004109 A1   Jan. 5, 2006

(51) Int. Cl.
   *C07C 213/02*   (2006.01)
(52) U.S. Cl. ............................................ 564/349
(58) Field of Classification Search ............ None
   See application file for complete search history.

(56) References Cited

U.S. PATENT DOCUMENTS

| | | | |
|---|---|---|---|
| 4,760,182 A * | 7/1988 | Ippolito et al. | 564/349 |
| 4,990,668 A * | 2/1991 | Mai et al. | 564/349 |
| 5,731,463 A * | 3/1998 | Wang et al. | 564/399 |
| 5,942,633 A * | 8/1999 | Wang et al. | 549/539 |

OTHER PUBLICATIONS

Manoury et al., Journal of Medicinal Chemistry (1987), 30(6), p. 1003-1011.*

Database CAPLUS on STN, Acc. No. 2004:825286, Rao et al., IN 184973 (Oct. 14, 2000) (abstract).*

* cited by examiner

*Primary Examiner*—Brian Davis
(74) *Attorney, Agent, or Firm*—Nixon & Vanderhye P.C.

(57) ABSTRACT

The present invention relates to an improved process for preparation of S-(−)-betaxolol salts. More particularly the present invention relates to the preparation of hydrochloride salt of S-(−)-betaxolol of formula (1)

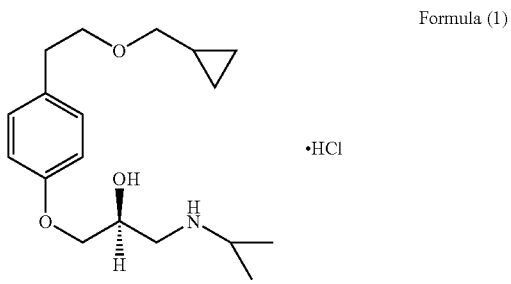

Formula (1)

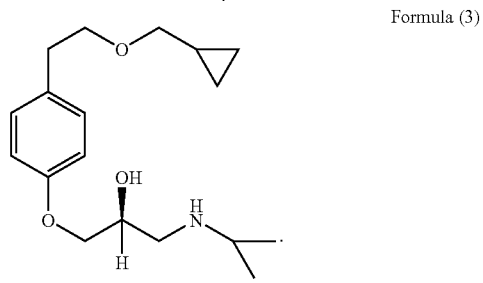

Formula (3)

10 Claims, No Drawings

PROCESS FOR PREPARATION OF S-(−)-BETAXOLOL AND SALTS THEREOF

FIELD OF THE INVENTION

The present invention relates to an improved process for preparation of S-(−)-betaxolol and salts thereof. More particularly the present invention relates to the preparation of hydrochloride salt of S-(−)-betaxolol of formula (1).

BACKGROUND OF THE INVENTION

Racemic betaxolol of formula (2) is a β-adrenoreceptor antagonist

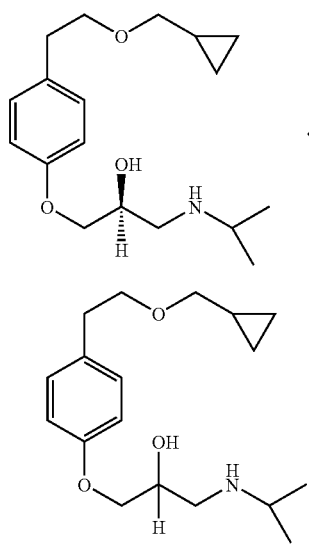

Formula (1)

Formula (2)

with a pharmacological and pharmacokinetic profile for the treatment of chronic cardiovascular diseases like glaucoma. The disease glaucoma is characterized by the progressive damage to the optic nerve caused by the increased pressure within the eye. Glaucoma is a serious disease of the eye, which may lead to the loss of peripheral vision and if untreated total blindness.

β-adrenoreceptor antagonist (β-blockers) are popularly used to lower intraoccular tension, other conditions of increased intraoccular pressure and management of essential hypertension. The principle effect of β-adrenoreceptor blocker is to reduce cardiac activity by diminishing or preventing β-adrenoreceptor stimulation i.e. by reducing the rate and force of contraction of the heart.

Betaxolol belongs to aryloxypropanolamine class of drugs having a specific action on the cardiovascular receptor sites. Most of the drugs in this series contain one chiral carbon centre but generally administered as racemates. Pharmacological studies have shown that an organism often reacts in a different way when it interacts with each enantiomer of the same molecule. This has promoted the growth of both the switch from the use of racemic drug to single enantiomer drug and innovation the manufacturing processes to make enantiomerically pure molecules with low cost. Although most of the β-blockers are sold as racemates, only S-isomer is associated with β-blocking activity, while the R-isomer is usually responsible for side effects. (Hussian S. S. et al, Toxiocol, 1989, 12)

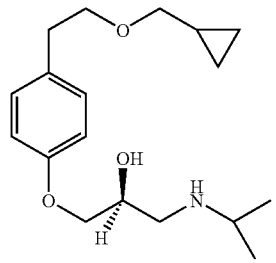

Formula (3)

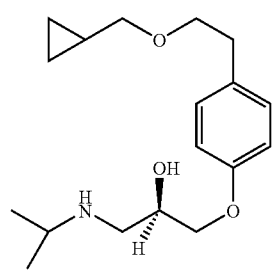

Formula (4)

The pharmacological characteristics of S-(−)-Betaxolol (Levobetaxolol) of formula (3), a single active isomer of betaxolol exhibited a higher affinity at cloned human β-1 than at β-2 receptors while R-(+)-Betaxolol (Dextrobetaxolol) of formula (4) was much weaker at both receptors. Levobetaxolol was 89-times β-1 selective vs. β-2. Levobetaxolol is more potent than Dextrobetaxolol at inhibiting isoproterenol induced CAMP production in human non-pigmented ciliary epithelial cells and exhibited a micro molar affinity for L-type $Ca^{2+}$ channels. In conclusion, levobetaxolol is a potent, high affinity and β-1 selective 10P lowering β1 adrenoreceptor antagonist.

Prior Art:

Synthesis of S-(−)-betaxolol of formula (3) has been reported by alkylation of phenol derivative with S-(−)-2-phenyl-3-isopropyl-5-hydroxymethyl oxazolidinyl tosylate of formula (12) followed by the acid catalysed hydrolysis (Philippe M. Manoury; Jean L. Binet; Jean Rousseau; *J. Med. Chem.* 1987, 30, 1003–1011).

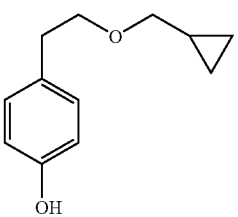

Formula (9)

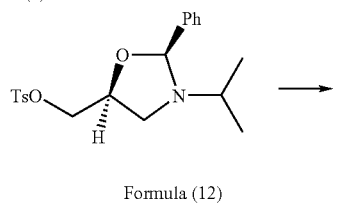

Formula (12)

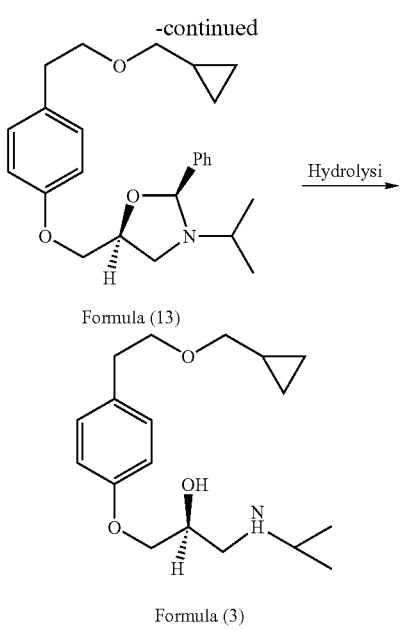

Formula (13)

Formula (3)

The enantiomers of betaxolol have been prepared via lipase catalysed kinetic resolution of racemic drug (Giuseppe Di Bono; Antonio Scilimuti; *Synthesis*, 699, June 1995). The racemic drug on treatment with acetic anhydride afforded N,O-bisacetylated derivative which was hydrolysed enantio-selectively using PPL or lipase K-10. Alternatively trans esterification reaction was performed using vinyl acetate as the acyl doner on the key intermediate 1-chloro-3-[4(2-cyclopropylmethoxy)ethyl]-phenoxy propan-2-ol.

Drawbacks:

The asymmetric synthesis starting from oxazolidinone derivative of formula (12) involves number of steps. R-glyceraldehyde is converted to the required oxazolidinone derivative in four steps. R-glyceraldehyde is not very stable compound and not commercially available, although it can be prepared from the cleavage of D-mannitol-1,2,5,6-bisacetonide on treatment with lead tetraacetate or sodium periodate among other methods.

The chemoenzymatic route involves either lipase catalyzed hydrolysis or transesterification but the optical purity up to 80% was noted which needs recrystallisation of hydrochloride to improve ee to ~90%. The overall yield is moderate up to 50%.

In both the above processes cyclopropylmethyl halide has been employed for introducing cyclopropyl group as a reactive intermediate. The cyclopropylmethyl halide is not expensive but highly lachrymetric and unstable. These limitations make the reported processes economically inviable and difficult to scale up.

There is therefore a need to develop an economically viable alternative process for S(−)-betaxolol and its hydrochloride salt wherein the use of cyclopropylmethyl halide is avoided and also product with improved enantiomeric purity.

OBJECTS OF THE INVENTION

The object of present invention therefore is to prepare salts of S-(−)-betaxolol with high enantiomeric purity and to avoid use of highly lacrymatric and unstable cyclopropylmethyl halide.

SUMMARY OF THE INVENTION

Accordingly the present invention provides an improved process for the preparation of S-(−)-betaxolol of the formula, (3) as fully illustrated in hereinafter which comprises following steps 1. Condensing 2-[4-hydroxyphenyl-ethanol] of formula, (5) with benzyl halide in the presence of a base, phase transfer catalyst and organic solvent to obtain 2-[4-benzyloxyphenyl-ethanol] of formula, (6).

2. Condensing 2-[4-benzyloxyphenyl-ethanol] of formula, (6) with an allyl halide in the presence of a base and an organic solvent to obtain 1-(2-allyloxyethyl)-4-benzyloxybenzene of formula, (7).

3. Cyclopropanating 1-(2-allyloxyethyl)-4-benzyloxybenzene of formula (7) by conventional methods such as Simmon smith reaction and Furukawa modification of Simmon smith reaction to obtain the 1-benzyloxy-4-(2-cyclopropyl methoxy-ethyl)-benzene of formula, (8).

4. Deprotecting 1-benzyloxy-4-(2-cyclopropylmethoxyethyl)-benzene of formula (8) by hydrogenation to obtain 4-(2-cyclopropylmethoxyethyl)-phenol of formula (9).

5. O-Alkylation of 4-(2-cyclopropylmethoxyethyl)-phenol of formula, (9) by treating with R-(−)-epichlorohydrin in the presence of alkali to obtain the mixture of compounds of the formulae (10+11); treating the mixture of compounds of the formulae, (10+11) with isopropylamine to give S-(−)-betaxolol of the formula, (3).

6. Treating S-(−)-betaxolol of the formula, (3) with alcoholic hydrochloric acid in organic solvent to give S-(−)-betaxolol HCl, of formula (1) or maleic acid in organic solvent to give S-(−)-betaxolol maleate salt.

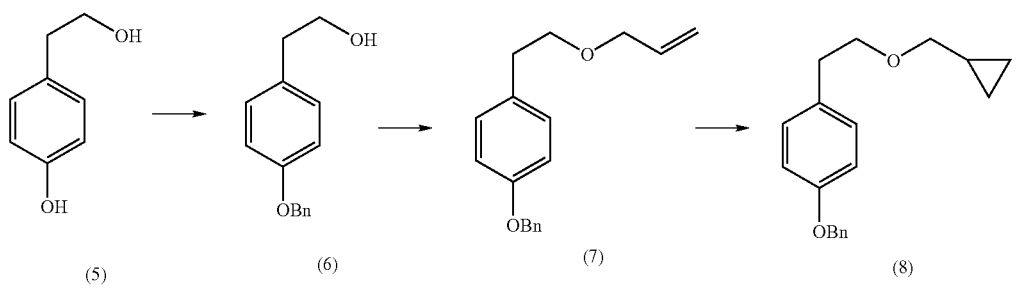

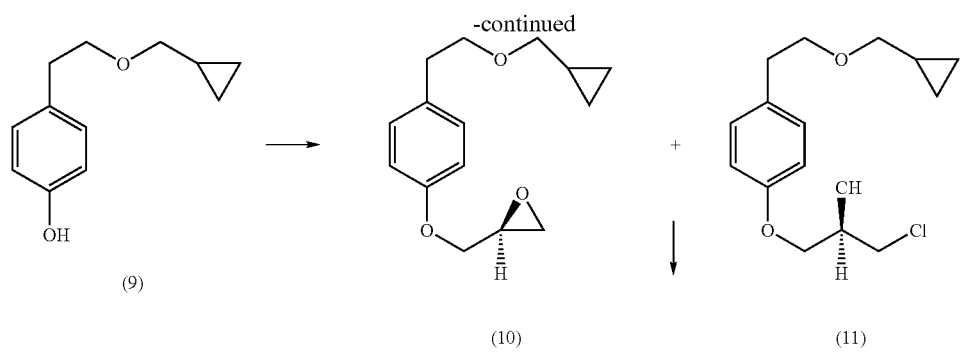

In one of the embodiments of the present invention base used in step (1) may be alkali metal carbonates such as carbonates of sodium, potassium or alkali metal hydroxides such as sodium, potassium.

In another embodiment organic solvent in step (1) may be aliphatic ketones such as acetone, methyl ethyl ketone, methyl isobutyl ketone or cyclic ethers.

In still another embodiment allyl halide used in step (2) may be chloride, bromide; bases used may be sodium hydride or potassium t-butoxide and solvents used for reaction may be ethereal solvent such as tetrahydrofuran or polar solvents such as DMSO, DMF.

In another embodiment cyclopropanation in step (3) may be obtained by Zn—Cu couple (Simmons Smith) or diethyl zinc in hexane (Furukuwa).

In yet another embodiment deprotection by hydrogenation in step (4) may be carried out using Raney Nickel or as in conventional method by Pd—C.

In still another embodiment alkali used in step (5) may be alkali hydroxides such as sodium hydroxide or potassium hydroxide.

In another embodiment solvent used for formation of hydrochloride salt of S(−) Betaxolol may be hydrocarbons such as toluene, cyclohexane and ethers: diisopropyl ether, diethyl ether.

DETAILED DESCRIPTION OF THE INVENTION

The present invention provides an improved process for the preparation of S-(−)-betaxolol of the formula, (3) as described below. The process of the invention comprises the steps of 1. Condensing 2-[4-hydroxyphenyl-ethanol] of formula, (5) with benzyl halide in the presence of a base, phase transfer catalyst and organic solvent to obtain 2-[4-benzyloxyphenyl-ethanol] of formula, (6).

2. Condensing 2-[4-benzyloxyphenyl-ethanol] of formula, (6) with an allyl halide in the presence of a base and an organic solvent to obtain 1-(2-allyloxyethyl)-4-benzyloxybenzene of formula, (7).

3. Cyclopropanating 1-(2-allyloxyethyl)-4-benzyloxybenzene of formula (7) by conventional methods such as Simmon smith reaction and Furukawa modification of Simmon smith reaction to obtain the 1-benzyloxy-4-(2-cyclopropyl methoxy-ethyl)-benzene of formula, (8).

4. Deprotecting 1-benzyloxy-4-(2-cyclopropylmethoxy-ethyl)-benzene of formula (8) by hydrogenation to obtain 4-(2-cyclopropylmethoxyethyl)-phenol of formula (9).

5. O-Alkylation of 4-(2-cyclopropylmethoxyethyl)-phenol of formula, (9) by treating with R-(−)-epichlorohydrin in the presence of alkali to obtain the mixture of compounds of the formulae (10+11); treating the mixture of compounds of the formulae, (10+11) with isopropylamine to give S-(−)-betaxolol of the formula, (3).

6. Treating S-(−)-betaxolol of the formula, (3) with alcoholic hydrochloric acid in organic solvent to give S-(−)-betaxolol HCl, of formula (1) or maleic acid in organic solvent to give S-(−)-betaxolol maleate salt.

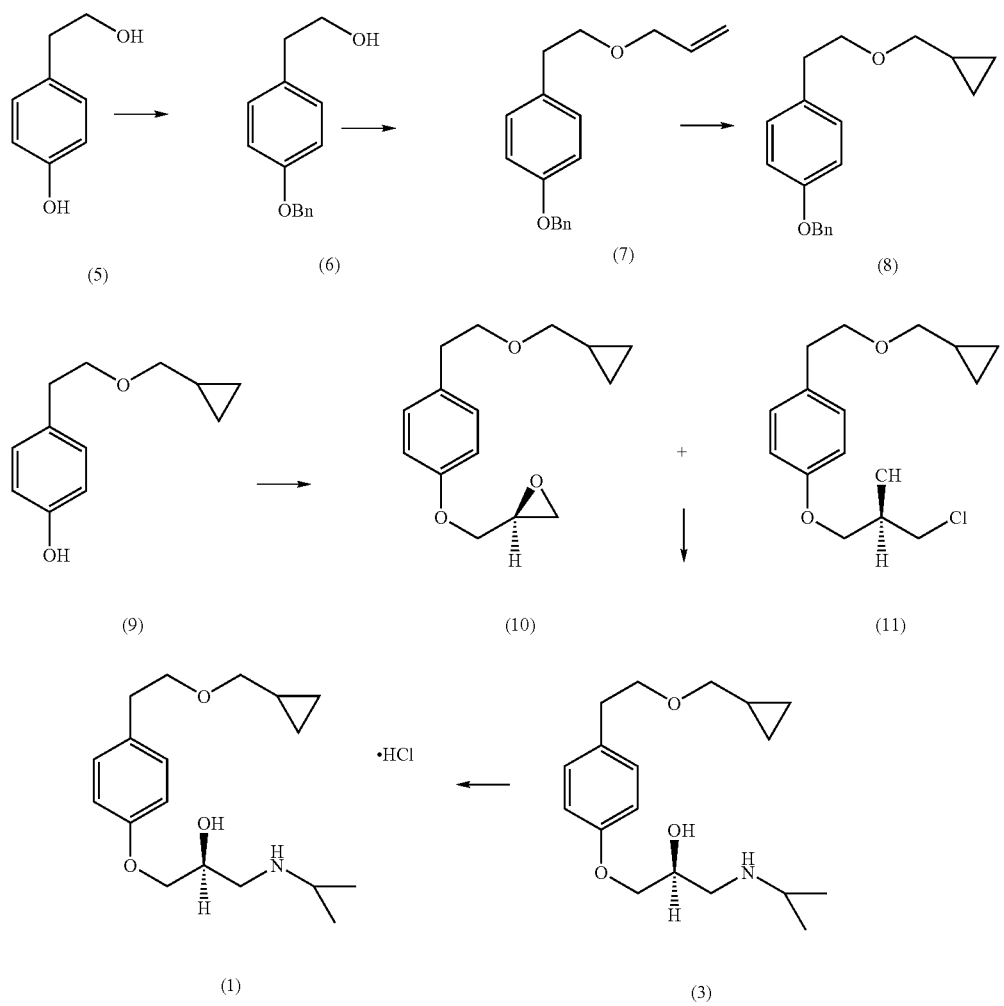

The base used in step (1) can be an alkali metal carbonate such as carbonates of sodium or potassium or alkali metal hydroxides such as hydroxides of sodium or potassium. The organic solvent in step (1) is preferably an aliphatic ketone such as acetone, methyl ethyl ketone and methyl isobutyl ketone or a cyclic ether. The allyl halide used in step (2) may be chloride, bromide; bases used may be sodium hydride or potassium t-butoxide and solvents used for reaction may be ethereal solvent such as tetrahydrofuran or polar solvents such as DMSO, DMF.

Cyclopropanation in step (3) may be obtained by Zn—Cu couple (Simmons Smith) or diethyl zinc in hexane (Furukuwa). Deprotection by hydrogenation in step (4) may be carried out using Raney Nickel or as in conventional method by Pd—C. The alkali used in step (5) may be alkali hydroxides such as sodium hydroxide or potassium hydroxide.

The solvent used for formation of hydrochloride salt of S(−) Betaxolol may be hydrocarbons such as toluene, cyclohexane and ethers: diisopropyl ether, diethyl ether.

The process of the present invention is described herein below with reference to the following examples, which are illustrative only and should not be construed to limit the scope of the present invention in any manner.

EXAMPLE I

This example describes the preparation of 4-benzyloxy-(2-phenethyl ethanol) of formula (6)

In a 250 ml reaction flask 2-(4-Hydroxyphenyl)-ethanol of formula, (5) (10 g, 0.07246 mol), potassium hydroxide (6.1 g, 0.1087 mol) and catalytic amount of phase transfer catalyst tetrabutyl ammonium bromide (0.150 g) was disssolved in 65 ml of THF. Stirred it for 1.5 hr. Benzyl bromide (8.6 ml, 0.07246 mol), was added to the reaction mixture dropwise. Stirred the reaction mixture at room temperature for 4 hrs. The progress of reaction was cheked by TLC. Filtered the reaction mixture and concentrated the filtrate on rota-vapour. The crude product was recrystalised from petroleum ether to afford 4-benzyloxy-(2-phenethyl ethanol) of formula (7), 14.9 g (90%) mp 85–86° C.

EXAMPLE II

This example describes the preparation of 1-(2-Allyloxyethyl)-4-benzyloxy benzene of formula (7)

To a stirred solution of alcohol of formula (6), (3 g, 0.013 mol) in dry THF (10 ml), Sodium hydride (60% dispersion in mineral oil, 0.95 g, 0.039 mol) was added portion wise at 0° C. The reaction mixture was stirred for 1 h at room temperature under nitrogen and then allyl bromide (2.4 g, 0.02 mol) was introduced. The reaction mixture was stirred for 15 h, at room temp, quenched with the addition of methanol. The solvent was removed and the residue partitioned between ethyl acetate and water. The organic layer was dried over anhydrous sodium sulphate, filtered and concentrated. The crude product was purified over silica gel column using ethyl acetate-light petroleum ether (1:33) as an eluent to afford compound of formula (6), as a colorless liquid 3 g (85%).

EXAMPLE III

This example describes the preparation of 1-(2-Allyloxyethyl)-4-benzyloxy benzene of formula (7)

A reaction flask was charged with 4-benzyloxy phenethyl alcohol of formula (6), (12 g, 0.052 mol), potassium tert-butoxide (8.842 g, 0.079 ml) and 50 ml and DMSO. The mixture was stirred under nitrogen at 50° C. for 30 minutes. A solution of allyl bromide (6.8 ml, 0.079 mol) was added drop wise to the reaction mixture with cooling about 20–25° C. The mixture was then stirred at 50° C. for 2 h. and cooled to room temperature. The reaction mixture was subsequently quenched with 150 ml of water. The desired product was extracted from neutralized aqueous mixture with toluene. The toluene extract was then washed with water and concentrated under vacuum to afford the title compound of formula (7), 13.9 g, (98%).

EXAMPLE IV

This example describes the preparation of 1-benzyloxy-4-(2-cyclopropylmethoxy-ethyl)-benzene of formula (8)

To a stirred solution of compound of formula (7), (12 g, 0.0447 mol) in dry hexane (50 ml), diethyl zinc (1.1 M solution in hexane, 185 ml) was added at 0° C. under nitrogen atmosphere followed by diiodomethane (18 ml, 0.224 mol). The reaction was stirred for 6 h at 0° C. and poured over cold aqueous solution of ammonium chloride. The organic layer was separated and the aqueous layer extracted repeatedly with diethyl ether. The combined organic layer was washed with aq. solution of sodium thiosulphate, dried over anhydrous sodium sulphate, filtered and concentrated. The crude product was purified over silica gel column using ethyl acetate and light petroleum ether (1:50) as an eluent to afford compound of formula (8), as a colorless liquid 11.365 g (90%).

EXAMPLE V

This example describes the preparation of 1-Benzyloxy-4-(2-cyclopropylmethoxy-ethyl)-benzene of formula (8)

To a suspension of Zn/Cu couple (3.24 g) and dry ether (20 ml) was added to the compound of formula (7), (2 g, 0.0075 mol) in ether (10 ml) followed by the addition of diiodomethane (4.2 ml, 0.052 mol). The reaction mixture was refluxed under nitrogen atmosphere for 72 h (monitored by TLC) and filtered. The filtrate was washed with water, dried, concentrated and the residue purified by column chromatography on silica gel, eluting with light petroleum ether:ethyl acetate(2:50) to afford pure product of formula (8), as an oil 1.8 g (85%).

EXAMPLE VI

This example describes the preparation of 4-(2-cyclopropylmethoxyethyl)phenol of formula (9)

The reported debenzylation procedure U.S. Pat. No. 4,348,783 using palladium charcoal was modified given as below.

A solution of compound of formula (8), (12 g) in methanol (100 ml) was stirred in presence of Raney-Nickel (10 ml slurry) under $H_2$ pressure (Parr Shaker 65-psi pressure). After 5 h the reaction mixture was filtered through a pad of cellite and the filtrate was concentrated. The crude product was purified by silica gel chromatography using ethyl acetate and light petroleum ether (1:9) as an eluent to afford compound of formula (9), as an oil 7 g (86%).

EXAMPLE VII

This example describes the preparation of S-(−)-Betaxolol of formula (3)

A solution of R-(−)-epichlorohydrin (3.855 g, 0.0417 mol) in water (2 ml) was stirred for 10 min. at 0–5° C. and the compound of formula (9), (5 g, 0.0261 mol), NaOH (1.146 g, 0.0287 mol) and benzyl triethyl ammonium chloride (catalytic amount) in water (16 ml) was added over a period of 1 h at 0° C. The reaction mixture was stirred for 80 h at 0° C., (monitored by TLC) and rendered acidic (pH=5) by addition of aqueous 3.5% HCl. To the reaction mixture isopropyl amine (38.5 ml, 0.651 mol) was added and stirred overnight at room temperature. The reaction mixture was concentrated and the residue extracted with chloroform and water. The organic layer was dried over sodium sulfate, concentrated on rota-vapour to afford 7.195 g (90%)chiral S-(−)Betaxolol of formula (3). ee>99 (determined by Chiral HPLC; Column-Chiracel OD 25 cm; mobile phase-hexane:isopropanol:diethyl amine (6:4:0.1); flow rate: 0.5 m/min; $\lambda_{max}$:228 nm).

$^1$H NMR: 0.20 (q, 2H, cyp); 0.53 (q, 2H, cyp); 1.07 (m, 1H, cyp); 1.08, 1.09 (2S, 6H, $(CH_3)_2N$); 2.69 (1H, CH—$CH_3$); 2.85 (m, 4H, $CH_2$—C, $CH_2$—O); 3.27 (d, 2H, O—$CH_2$); 3.61 (t, 3H, CH—O); 3.95 (d, 2H, $CH_2$—O); 4 (m, 1H, CH—OH); 6.85, 7.16 ($A_2B_2$, 4H, aromatic); Mass: $M^+$=307.

EXAMPLE VIII

This example describes the preparation of Maleate salt of S-(−)-Betaxolol

S-(−)-betaxolol of formula (3) (7.850 g, 0.02557 mol) was dissolved in ether (50 ml) and maleic acid (2.671 g, 0.023 mol) was added to this, stirred for 1 hr. White solid filtered to get maleate salt of S (−)-betaxolol 7.575 g (70%). mp 95–97° C. (Lit. mp 96–97° C.); Specific rotation $[\alpha]^{22}_D$–16.33. (Lit $[\alpha]^{22}_D$–14.9) (C=2.4, $CH_3OH$).

EXAMPLE IX

This example describes the preparation of hydrochloride salt of S-(−)-betaxolol of formula (1)

To a solution of S-(−)-Betaxolol of formula (3) (2.50 g) in 15 ml of toluene, Isopropanol-HCl (1 eq) (5 ml) was added dropwise under nitrogen atmosphere with stirring. Stirred for 1 h. Concentrated and again added 5 ml of toluene stirred for 15 min. This process was repeated for two times. Finally removed the solvent completely and diethyl ether added to precipitate S-(−)-betaxolol hydrochloride of formula (1), as a solid. Filtered it under nitrogen atmosphere 2.66 g (95%), mp 92–93° C.;

Specific rotation $[\alpha]^{22}_D$ −13.46 (C=2, CHCl$_3$)

$^1$H NMR: 0.20 (q, 2H, cyp); 0.53 (q, 2H, cyp); 1.05 (m, 1H, cyp); 1.44, 1.66 (2S, 6H, (CH$_3$)$_2$N); 3.16 (m, 1H, CH—CH$_3$); 2.84 (t, 2H, CH$_2$—C); 3.28 (d, 2H, O—CH$_2$); 3.45 (m, 2H, CH$_2$—C); 3.59 (t, 3H, CH—O); 3.97, 4.05 (dd, 2H, CH$_2$—O); 4.61 (m, 1H, CH—O); 6.75, 7.06 (A$_2$B$_2$, 4H, aromatic); 8.51 (bs, 1H, NH); 9.56 (bs, 1H, NH).

EXAMPLE X

This example describes the preparation of hydrochloride salt of S-(−)-betaxolol of formula (1)

To a solution of S-(−)-Betaxolol of formula (3), (2.50 g) in 15 ml of ether, Isopropanol-HCl (1 eq) (5 ml) was added dropwise with stirring. Stirred for 1 h. Filtered the S-(−)-betaxolol hydrochloride salt of formula (1) as a white solid. 2.66 g (95%). mp 92–93° C.

Specific rotation $[\alpha]^{22}_D$ −13.46 (C=2, CHCl$_3$)

Advantages:

The process describes for the first time in detail the preparation of S(−)Betaxolol hydrochloride salt in good chemical yields and high enantiomeric purity using chiral epichlorohydrin.

We claim:

1. A process for the preparation of S-(−)-betaxolol of the formula (3) and hydrochloride or maleate salt of the formula (1) which comprises

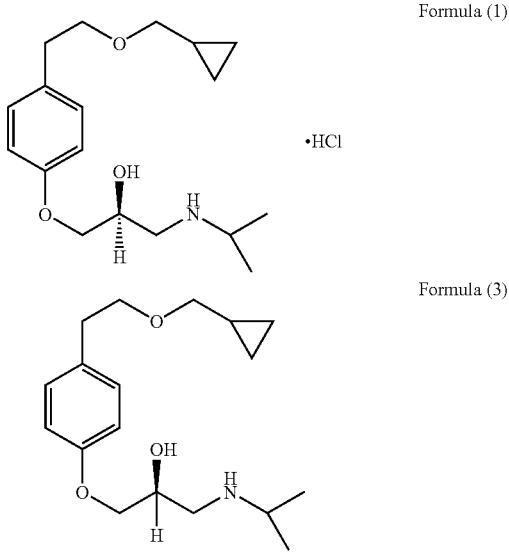

a. selectively benzylating 2-[4-hydroxyphenyl-ethanol] with benzyl halide in the presence of base and an organic solvent to obtain 2-[4-benzyloxyphenyl-ethanol];

b. condensing 2-[4-benzyloxyphenyl-ethanol] with an allyl halide in the presence of a base and an organic solvent to obtain 1-(2-allyloxyethyl)-4-benzyloxybenzene;

c. cyclopropanating 1-(2-allyloxyethyl)-4-benzyloxybenzene to obtain the 1-benzyloxy-4-(2-cyclopropyl methoxy-ethyl)-benzene;

d. deprotecting 1-benzyloxy-4-(2-cyclopropylmethoxyethyl)-benzene by hydrogenation to obtain 4-(2-cyclopropylmethoxyethyl)-phenol;

e. O-Alkylating the 4-(2-cyclopropylmethoxyethyl)-phenol to S(−)-betaxolol by treating with R-(−)-epichlorohydrin in the presence of alkali to obtain a mixture of compounds and treating the mixture with isopropylamine to give S-(−)-betaxolol of formula 3, and if desired f. treating S-(−)-betaxolol with alcoholic hydrochloric acid in organic solvent to give S-(−)-betaxolol HCl, or maleic acid in organic solvent to give S-(−)-betaxolol maleate salt.

2. A process as claimed in claim 1 wherein the base used in step (a) is an alkali metal carbonate selected from the group consisting of carbonates of sodium and potassium.

3. A process as claimed in claim 1 wherein the base used in step (a) is an alkali hydroxide selected from the group consisting of hydroxides of sodium and potassium.

4. A process as claimed in claim 1 wherein organic solvent in step (a) is an aliphatic ketone selected from the group consisting of acetone, methyl ethyl ketone and methyl isobutyl ketone.

5. A process as claimed in claim 1 wherein organic solvent in step (a) is a cyclic ether.

6. A process as claimed in claim 1 wherein allyl halide used in step (b) is selected from a chloride and a bromide, the base used is selected from sodium hydride and potassium t-butoxide and the solvent used is an ethereal solvent selected from the group consisting of tetrahydrofuran and a polar solvent selected in turn from the group consisting of DMSO, DMF.

7. A process as claimed in claim 1 wherein cyclopropanation in step (c) is carried out with diiodomethane by Zn—Cu couple (Simmons Smith) or diethyl zinc in hexane Furukawa).

8. A process as claimed in claim 1 wherein deprotection by hydrogenation in step (d) is carried out using Raney Nickel or by Pd—C.

9. A process as claimed in claim 1 wherein the alkali used in step (e) is an alkali hydroxide selected from sodium hydroxide and potassium hydroxide.

10. A process as claimed in claim 1 wherein the solvent used for formation of hydrochloride salt of S(−)Betaxolol is a hydrocarbon selected from the group consisting of toluene, cyclohexane and ethers selected in turn from the group consisting of diisopropyl ether and diethyl ether.

* * * * *